United States Patent [19]

Taback et al.

[11] 4,286,209

[45] Aug. 25, 1981

[54] SMALL CONDUCTIVE PARTICLE SENSOR

[76] Inventors: Israel Taback, Newport News, Va.;
Robert A. Frosch, Administrator of the National Aeronautics and Space Administration, with respect to an invention of Israel Taback

[21] Appl. No.: 70,366

[22] Filed: Aug. 28, 1979

[51] Int. Cl.³ .................................................. G01N 27/00
[52] U.S. Cl. ........................... 324/71 CP; 235/92 PC
[58] Field of Search ............ 235/92 PC; 324/71 CP; 73/28, 23, 194 F

[56]  References Cited

U.S. PATENT DOCUMENTS

| | | | |
|---|---|---|---|
| 2,262,370 | 11/1941 | Penney | 324/71 CP |
| 3,679,973 | 7/1972 | Smith | 324/71 CP |
| 3,718,029 | 2/1973 | Gourdine | 324/71 PC |

Primary Examiner—Michael J. Tokar
Attorney, Agent, or Firm—Howard J. Osborn; John R. Manning; William H. King

[57] ABSTRACT

This invention is an electrostatic conductive fiber detector for use in detecting, counting and measuring the length of fibers down to 0.1 mm and below with increased accuracy and reliability over prior art devices. It can be used for detection of fibers suspending in a flowing gas, in a nonflowing gas, or in a vacuum and its accumulated counts over a period of time is essentially unaffected by velocity of the fibers being detected.

3 Claims, 2 Drawing Figures

SMALL CONDUCTIVE PARTICLE SENSOR

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

This invention relates generally to means for detecting particulate matter and more specifically to an improved electrostatic small conductive fiber detector which can reliably sense particulate fibers 2 mm or less in length.

A prior art device consisting of a 1.5 inch diameter metallic sphere charged to a high DC potential is used to generate an electrostatic field such that whenever a fiber falls within the influence of the electrostatic field, it is converted into a dipole and is radially aligned and attracted to the spherical sensor. As the attracted fiber contacts the sphere, it is charged to a like potential and repelled. The charge removed from the sphere is sensed, amplified and shaped into a pulse whose magnitude is a function of fiber length. The pulse can then be stored in an appropriate memory device, and analyzed to give total fiber count per unit time, fiber length spectrum over a specified period, and various other functions relating fiber count, fiber length, and time as desired. This device is accurate and reliable in detecting and measuring fibers with lengths ranging from 3 mm to 12 mm.

Applications requiring accurate fiber count and length measurement of fibers 2 mm or less in length have been difficult if not impossible using the spherical sensor device of the prior art. This is due mainly to the inability to differentiate the small charge pulse transferred to a short fiber from electromagnetic interference and electronic background noise. An improvement in sensitivity of the prior art device was achieved by utilizing two spherical sensor units connected through a differential amplifier. The differential amplifier had high common mode rejection and thus eliminated interference common to both sensors allowing fibers with length as short as 1 mm to be detected. This method, however, required a duplication of sensors and associated equipment, and the addition of a high gain, common mode rejection differential amplifier to the circuit. Also, although it does give an improvement in sensitivity, the improved length detection spectrum is not sufficient for many purposes. Another means of increasing sensor sensitivity is decreasing the diameter of the sphere. This results in a larger charge being transferred to a fiber upon contact, but the decrease in spherical sensor diameter also results in a corresponding decrease in the effective capture area of the electrostatic field around the sensor. The reduction in capture area causes a corresponding reduction in fiber counts per unit time. Although the pulse size for a small fiber increases, the number of pulses caused by fibers decreases in relation to the number of similar amplitude pulses from electromagnetic and electronic interference and noise, which remain essentially constant, with a resultant decrease in the accuracy of detection.

It is therefore an object of this invention to provide an electrostatic particle detector that can detect, count and measure the length of small conductive fibers.

Another object of this invention is to provide an electrostatic small conductive particle detector using a minimum of components.

A further object of this invention is the provision of an electrostatic small conductive particle detector having increased sensitivity to small fibers while retaining a large capture area.

Still another object of this invention is to provide an electrostatic small conductive particle detector allowing sensor selection such that particle size sensitivity can be varied to detect a desired size range of particles while retaining a large capture area.

Yet another object of this invention is to provide an electrostatic small conductive particle detector whose sensing element can be formed into grids of large area while retaining small fiber sensitivity.

A still further object of this invention is to provide an electrostatic small conductive particle detector which can be used to detect particles entrained in a flowing gaseous medium, dispersed in a nonflowing gaseous medium, or dispersed in a vacuum.

Another object of the invention is to provide a detector which can determine concentrations of varying length conductive fiber particles per unit volume over a period of time.

Other objects and advantages of this invention will become apparent hereinafter in the specification and drawings.

SUMMARY OF THE INVENTION

The invention consists essentially of a wire of diameter x and length y which is charged by a high DC voltage such that it creates a nonuniform electrostatic field. When a conductive fiber comes within the influence of the electrostatic field, it becomes a dipole and is radially aligned and attracted to the wire. When the fiber contacts the wire, it is charged to a like potential. The amount of charge taken from the wire is sensed, amplified, and shaped into a pulse, and input to a multichannel analyzer which counts and sorts the pulse according to its magnitude. The fiber now charged to the same potential as the wire is repelled clear of the detector. The operation of the wire sensor is essentially identical to the above described spherical sensor type detector with the important difference that by decreasing the diameter x of the wire, it becomes more sensitive to small fibers. The smaller the wire diameter used, the smaller the fibers that can be detected. An improvement in sensitivity to individual fibers is achieved comparable to that achieved by reduction in sphere diameter described above. As the wire diameter is decreased the length of the wire sensor can be increased thus maintaining desired capture area and preserving accuracy.

DETAILED DESCRIPTION OF THE INVENTION

Figure 1:
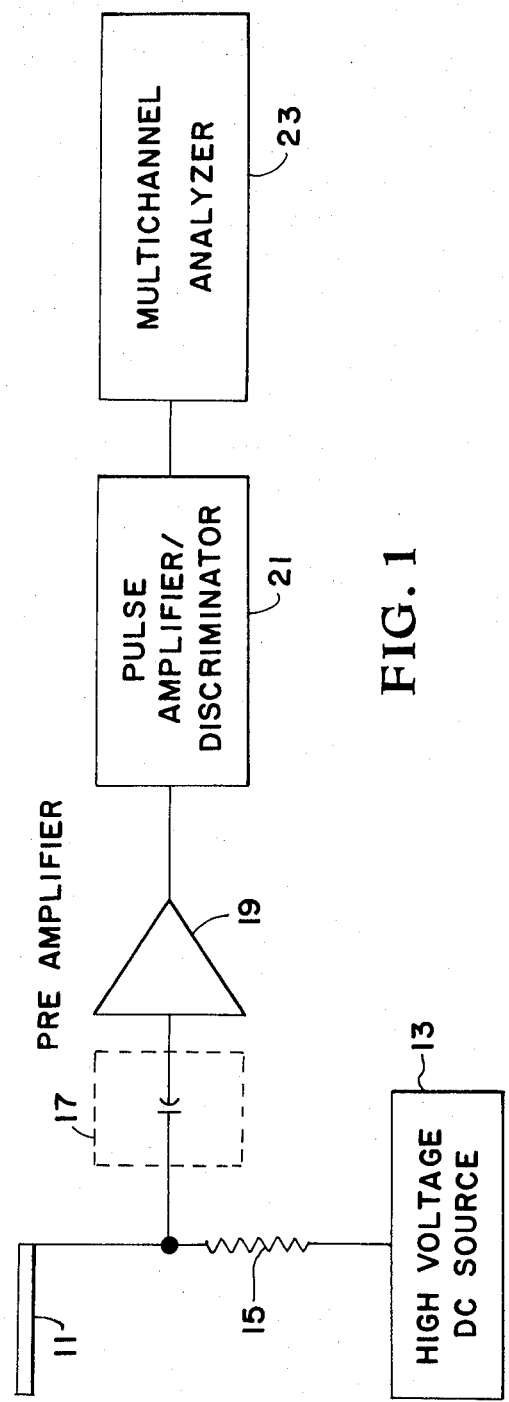
FIG. 1 is partly a block diagram and partly a circuit diagram of an apparatus embodying the principals of the invention.

The embodiment of the invention selected for illustration in the drawings is shown in FIG. 1. Wire sensor 11, an AWG 24 copper wire with a circular cross-section of approximately 0.020 inch and length of six inches, is charged by a 1500 VDC source 13 through load resistor 15 having a value of 2.2 megohms. An electrostatic field is generated by the charged wire 11, which attracts and radially aligns conductive fibers that pass within its influence. As the fiber contacts the wire sensor 11 the fiber removes a charge from the wire resulting in a voltage pulse caused by the potential drop across the load resistor 15. The fiber now charged to a like potential is repelled from the wire 11.

The fiber created pulse signal generated at the wire 11 is passed through a DC voltage isolating coupling means 17, which in the illustrated embodiment is a 0.01 μf capacitor coupling, but may be any coupling means which will isolate the constant high voltage DC source 13 from the counting means, and pass the high frequency AC signal pulse; e.g., a high frequency transformer coupling. The output signal can then be utilized by any appropriate counting means to suit the desired application. In the illustrated embodiment, the signal is passed to a preamplifier 19 having unity voltage gain which drives the instrumentation cable. Incorporated in the preamplifier 19 is a high voltage input and current limit resistor and also a test input for system checkout and calibration. The signal passes from the preamplifier 19 to a pulse amplifier and discriminator 21 which provides low level noise discrimination, amplification and pulse shaping. The signal is then sent to an appropriate analyzation and memory or recording device such as the multichannel analyzer 23 of the illustrated embodiment. In the multichannel analyzer 23, the fiber data can be stored and read out as a function of fiber length forming a fiber length spectrum giving concentrations of fibers of each length collected over the entire sampling period, or it can be read out as a function of time giving a fiber concentration versus time display. All of the components illustrated are commercially available, and familiar to those skilled in the art. The precise values and functions of any one of them may be varied to provide the desired output in accordance with particular applications.

Sensor wire 11 may be of any conductive material, even those having very low conductivity. The sensor material can accordingly be chosen for corrosion resistance, temperature compatability or other desired attributes, independent of conductivity. The conductivity of the sensor wire 11 can vary in a wide range with only slight affect to signal pulse shape. Similarly, the conductivity of detectable fibers can vary from highly conductive fibers such as gold to fibers having a resistivity of several megohms per cm. Tests with high resistance carbon carrying fibers and soot particles successfully demonstrated operability virtually independent of fiber conductivity. Sensor wire 11 diameter and length may be varied as desired to give required sensitivity and capture area of the field, but the cross-section must remain circular to provide an accurate relation between generated pulse magnitude and fiber length.

The values of the high voltage DC source 13 and the load resistor 15 are chosen to provide optimum detection for the fiber size and type and the number of counts per second expected. Field strength and thus signal pulse strength is a function of DC voltage applied to wire 11. The illustrated embodiment uses an operating voltage of 1500 VDC, as it provides the largest practical signal pulse without creating unnecessary noise sources from local voltage breakdown at connectors and other sharp-edged, field-enhancing elements of the circuitry as voltage increases. The voltage may be varied significantly depending upon desired application, and at least through a range of approximately 500 VDC to 2000 VDC.

Similarly the load resistor 15 is chosen to provide the greatest potential difference at the instant of fiber contact to create a correspondingly large signal pulse. This is accomplished by making resistance 15 as large as possible, but not so large as to significantly affect sensor recovery time, which is increased as resistor 15 value is increased. Although a resistor 15 value of 2.2 megohms was chosen in the illustrated embodiment for use in detecting graphite fibers, resistor 15 value could be matched with DC voltage source 13 to provide optimum conditions for other applications and could vary at least within the range of approximately 500 kilohm to 10 megohms.

The advantages of wire sensor 11 over the spherical sensor of the prior art are a result of the fact that the strength of the electrostatic field generated about wire sensor 11, varies inversely as the distance to the center of the wire 11, and is independent of wire 11 length. Whenever a conductive fiber passes within the influence of said electrostatic field it becomes a dipole which is radially aligned and attracted to the sensor wire 11. As the fiber contacts the sensor wire 11 the fiber withdraws a number of electrons proportional to the strength of the field at that location. The smaller the diameter of the sensing wire 11 the closer a contacting fiber can come to the center of the wire 11 and correspondingly the greater the charge it can then remove. Small fibers, on the order of 2 mm and below, remove proportionally less charge from any given sensor than do longer fibers. For example, using a 1.5 inch diameter sphere as the sensor and charging it to 1500 VDC through a 2.2 megohm load resistor, a 2 mm graphite fiber impact will result in a 7.2 mv signal pulse while a 1 mm graphite fiber will produce only a 1.25 mv signal. The low amplitude of these signals make detection over interference and background noise virtually impossible. If, however, a six-inch length of #24 conductive wire is substituted as the sensor in place of the ball, and all other parameters remain the same, the same 2 mm fiber will create a 100 mv pulse and the 1 mm fiber will provide a 40 mv pulse, both pulses are of relatively large magnitude and easily read out of the background noise. The improved signal strength obtained by the use of wire 11 in place of the sphere is due to the fact that the diameter of the #24 wire is approximately 0.020 inch and when any fiber contacts the wire it is only 0.010 inches away from the center of the wire which is the point of greatest field strength. The same fiber contacting the sphere is 0.75 inches from the center of the sphere, the field strength is correspondingly less, and the resultant charge transfer is also less, yet the wire 11 has the same detection cross-section as the ball because its length, which is independent of field strength, can be adjusted to ensure that an adequate detection cross-section is maintained. A spherical sensor reduced to 0.020 inch diameter would have the same sensitivity to small fibers as the 0.020 inch wire, but the sphere would have a collection cross-section almost two orders of magnitude smaller than the six-inch wire sensor. It is clear that by using sensor wire 11 in place of the prior art spherical sensor, the wire diameter may be varied to provide improved sensitivity to small fibers and yet retain, by adjusting length, a relatively large detection cross-section ensuring an adequate number of fibers is collected per unit time to provide accurate measurement. Smaller diameters of wire 11 can be selected as needed for smaller fiber detection. Sensitivity to fiber lengths of about 0.1 mm has been successfully demonstrated and detection of even shorter fibers is possible through the use of smaller diameter wires and by proper selection of charging voltage 13 and load resistance 15.

The wire sensor 11 is not affected by change in velocity of the fibers because the effective capture area of the wire 11 varies approximately in inverse proportion to the velocity of the fibers. Regardless of the velocity of the fibers, the accumulated counts over a period of time will remain virtually constant. The invention is therefore effective in detecting, counting, and measuring fibers regardless of whether the fibers are suspended in a bounded gas flow, suspended or free falling in a non-flowing gas, or suspended or free falling in a vacuum.

Figure 2:
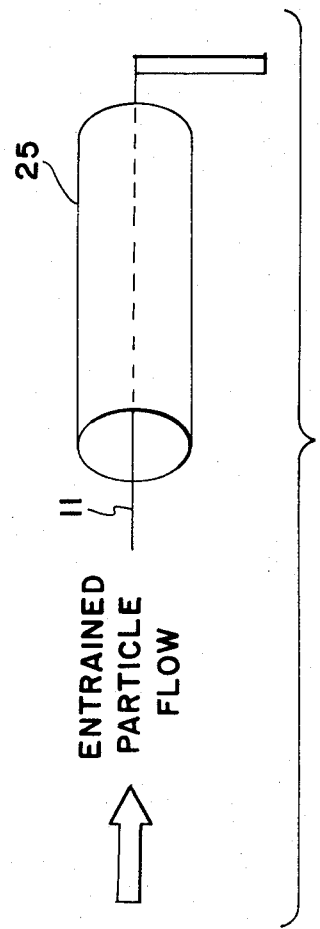
FIG. 2 is a pictorial view of an alternate embodiment of the wire sensor element of the invention.

FIG. 2 illustrates an alternative embodiment of the sensor element for use in detecting particles entrained in a bounded flow. This configuration is particularly suited to air sampling applications for detection of particulate emissions as would be present in stack gases. The sensor wire 11 is suspended in the center of a hollow conductive cylindrical member 25. A gas flow having entrained particles is introduced into one end of the cylindrical member 25 and the particles will be attracted by the electrostatic field of the wire 11, contact said wire, be charged and repelled; the repelled particle will strike the cylinder 25, be discharged, reattracted to the wire and so on as the particle passes through the cylindrical member. At each transit of the fiber between the cylinder 25 and wire 11 a charge transfer will take place. Each fiber will thus be counted a number of times as the gas sample flows through the cylinder 25 providing a greater signal-to-noise ratio. Because the wire sensor's electrostatic field is entirely contained within the cylinder 25 a great degree of electrical noise isolation can be achieved providing improved noise immunity, more counts per fiber, and an equivalent output pulse for a given fiber length as that provided by the plain wire sensor. The sensor element output would also be essentially independent of gas velocity because as the gas velocity increases the number of counts per fiber will decrease, however, the decrease will be proportionally offset by the increased number of particles available to be counted per unit time due to the increased flow.

Other embodiments of the invention could feature wire sensor 11 formed into collecting patterns of relatively large area for certain applications. Obviously many modifications and variations of the present invention are possible in the light of the above teachings, and may be made without departing from the spirit and the scope of the invention as set forth in the appended claims.

What is claimed as new and desired to be secured by Letters Patent of the United States is:

1. A device for detecting conductive particles, counting them, measuring their length, and determining the concentrations of different length particles per unit volume over a period of time comprising:
   a sensor wire made of an electrically conductive material;
   a high voltage DC source and a load resistor connected in series with said sensor wire for charging said wire to a high DC voltage whereby whenever a conductive fiber touches said wire the fiber becomes charged thereby removing part of the charge from said wire; and
   means for detecting the discharges of said wire wherein said detecting means is electrically connected between said sensor wire and said load resistor by a coupling means for isolating the direct current constant voltage of the source from the detecting means and passing the high frequency AC pulse signal generated by a fiber touching said wire to said detecting means.

2. The device of claim 1 including a hollow conductive cylinder and means of suspending said sensor wire concentric to and electrically isolated from said cylinder.

3. The device of claim 1 wherein said means for detecting includes means of counting and measuring the magnitude of said discharges whereby the number and lengths of said touching fibers are determined.

* * * * *